(12) United States Patent
Sullivan et al.

(10) Patent No.: US 6,370,962 B1
(45) Date of Patent: Apr. 16, 2002

(54) DYNAMIC HIGH SPEED TENSILE TESTER

(75) Inventors: John L. Sullivan, Ft. Salonga; Jeffrey J. Bott, Setauket, both of NY (US)

(73) Assignee: Testing Machines, Inc., Islandia, NY (US)

( * ) Notice: Subject to any disclaimer, the term of this patent is extended or adjusted under 35 U.S.C. 154(b) by 0 days.

(21) Appl. No.: 09/594,135

(22) Filed: Jun. 14, 2000

(51) Int. Cl.⁷ .................................................. G01N 3/08
(52) U.S. Cl. ........................................... 73/826; 73/833
(58) Field of Search ........................... 73/826, 862.391, 73/833, 862.42; 33/813, 815

(56) References Cited

U.S. PATENT DOCUMENTS

| | | | |
|---|---|---|---|
| 2,677,187 A | 5/1954 | Buist et al. | |
| 3,721,119 A | 3/1973 | Strimel | |
| 3,803,907 A | 4/1974 | Ryckman et al. | |
| 3,904,234 A | * 9/1975 | Hill et al. | 294/106 |
| 4,909,084 A | 3/1990 | Knoff | |
| 5,224,386 A | * 7/1993 | Curtis | 73/833 |
| 5,265,476 A | * 11/1993 | Khachaturian et al. | 73/828 |
| 5,351,553 A | 10/1994 | Lepie et al. | |
| 5,431,060 A | * 7/1995 | Lauren | 73/831 |
| 5,437,192 A | 8/1995 | Kawamoto et al. | |
| 5,598,738 A | * 2/1997 | Buescher, Jr. et al. | 73/761 |
| 5,693,890 A | * 12/1997 | Holmes | 73/856 |
| 5,767,402 A | * 6/1998 | Sandlass et al. | 73/779 |
| 5,911,166 A | * 6/1999 | Cowan | 73/833 |
| 6,041,660 A | * 3/2000 | Fujitaka et al. | 73/826 |
| 6,148,676 A | * 11/2000 | Bergs | 73/833 |
| 6,176,141 B1 | * 1/2001 | Ericson | 73/856 |

* cited by examiner

Primary Examiner—Benjamin R. Fuller
Assistant Examiner—Andre Allen
(74) Attorney, Agent, or Firm—Anthony J. Casella; Gerald E. Hespos

(57) ABSTRACT

A system is provided for determining the tensile characteristics of a sample under dynamic conditions. The system includes an apparatus adapted to accelerate the sample to a desired test velocity and maintain the test velocity through a predetermined test run, and a microprocessor for controlling the apparatus, data collection and data evaluation. The apparatus is formed with two movable clamping jaws for engaging the sample and sensors for measuring characteristics necessary to determine the stress-strain characteristics of the sample. During the course of the test, a sample is accelerated to a predetermined test velocity and one end of the sample is caused to be instantaneously fixed. The other end of the sample is then translated away from the fixed end at the test velocity. A closed loop between the microprocessor, a linear encoder measuring velocity, and a linear motor can be formed to accordingly adjust and maintain the desired test velocity.

20 Claims, 4 Drawing Sheets

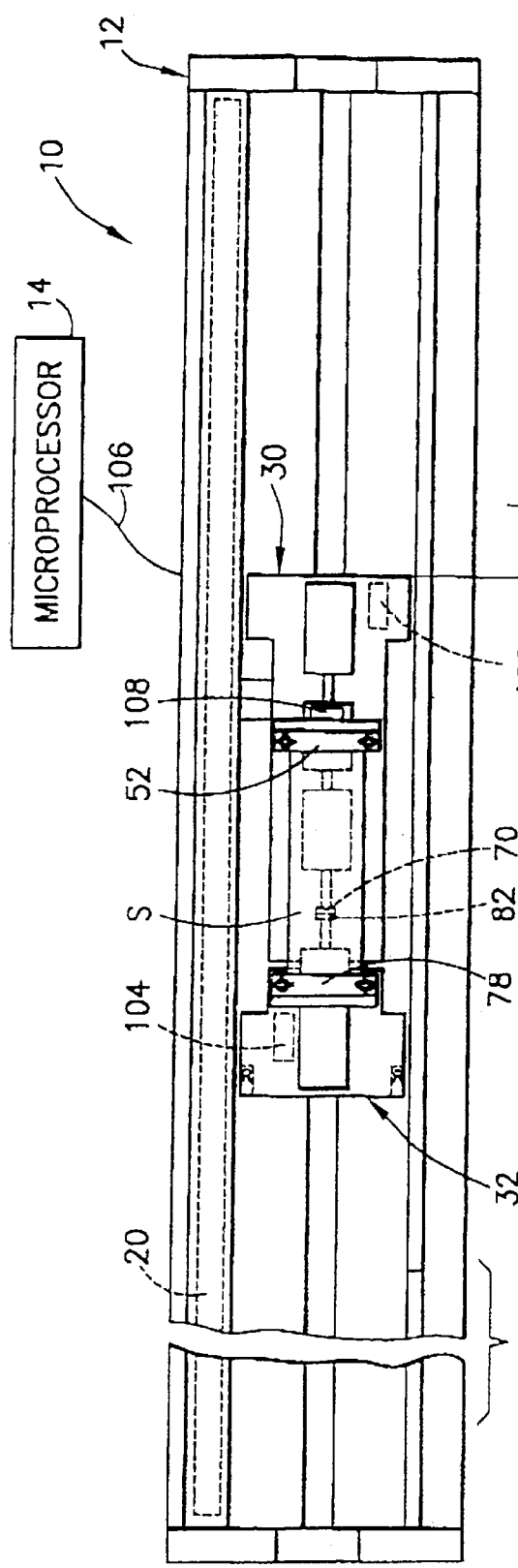
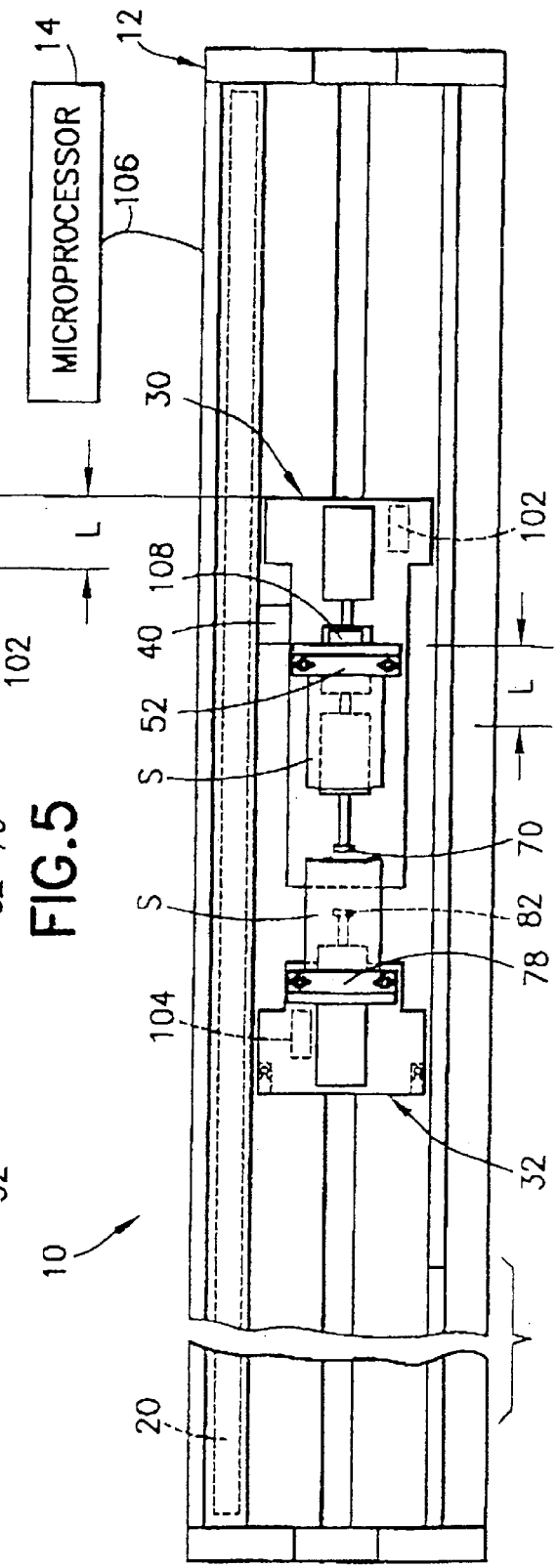

DYNAMIC HIGH SPEED TENSILE TESTER

BACKGROUND OF THE INVENTION

1. Field of the Invention

This invention relates to tensile testing apparatuses and more particularly, tensile testing apparatuses which simulate dynamic conditions.

2. Description of the Prior Art

Tensile testers are known in the prior art which can test and evaluate the tensile strength of a sample of sheet material or fiber under static conditions. An example of such a prior art device is sold by the assignee herein under the tradename "MICRO 350 UNIVERSAL TESTER." This apparatus is provided with two jaws, one being stationary and the second being movable, to grip opposing ends of a sample. The sample is engaged at opposing ends, with the entire assembly of the jaws and sample being stationary at the onset of a test. In conducting the test, the movable jaw moves away from the stationary jaw until the sample fails. During the course of the test, measurements of stress and strain are made and the tensile characteristics of the sample are determined.

It has been determined that tensile properties of certain materials, such as paper, change when placed under dynamic conditions. In particular, it has been found that the modulus of elasticity of certain materials varies with the sample travelling at various velocities. Consequently, the elasticity/brittleness of the sample can be considered a function of the velocity the sample is travelling when placed under tensile load. For example, a sheet of paper passing through a photocopying machine is forced to pass over a fusing roll which heats the sheet and causes curling thereof. To remove the curl, the sheet is quickly passed over a de-curling bar. While passing over the de-curling bar, the sheet of paper is subjected to tensile loading. It has been uncovered that with a sheet of paper moving, i.e. being under dynamic conditions, the tensile characteristics of the sheet of paper vary from that measured with the static procedure described above. As can be readily appreciated, the determination of dynamic tensile properties of a sample would allow a designer to properly take account of changing tensile properties. For example, the shape, angles of engagement and the rate of engagement of the sheet of paper with the de-curling bar can be properly designed for to allow the sheet to pass as quickly as possible over the de-curling bar without failing. At present, designers often take iterative steps to determine acceptable design criteria of the de-curling procedure.

It is an object of the subject invention to provide an apparatus for testing tensile properties of a sample under dynamic conditions.

SUMMARY OF THE INVENTION

The aforementioned object is met by a system for testing the tensile characteristics of a sample under dynamic conditions. In particular, the system includes an apparatus adapted to accelerate the sample to a desired test speed and maintain the test speed through a predetermined test run, and a microprocessor for controlling the apparatus, data collection and data evaluation. Generally, the apparatus includes an elongated housing, a rail mounted to the housing, two jaw assemblies mounted to the rail for translation along the length thereof, and a linear motor for driving one of the jaw assemblies.

The apparatus may be used to test the tensile properties of any sheet material, including paper, foil, plastic, and the like, as well as individual strands, filaments, and threads. Each of the jaw assemblies is formed with a clamping jaw for gripping one end of the sample. The jaw assemblies include a leading jaw assembly and a follower jaw assembly, wherein a detachable coupling is provided for forming a connection therebetween. The linear motor is mechanically connected to the leading jaw assembly. The follower jaw assembly is also driven by the linear motor, due to the connection to the leading jaw assembly formed by the detachable coupling.

Prior to conducting a test, a particular length of the rail is pre-designated as the length of a test run. In conducting a test run as described below, the linear motor must accelerate the jaw assemblies to the desired test speed upon entering the test run. To ensure the test speed has been achieved, the apparatus is configured to reach the test speed prior to entering the test run. At the initial point of the test run, a catch mechanism is provided for instantaneously stopping the follower jaw assembly. It is desired that the catch mechanism completely halt all subsequent movement and rebounding of the follower jaw assembly upon engagement therewith.

Two linear encoders are mounted to the jaw assemblies to allow for observation of various characteristics of the jaw assemblies. In particular, the velocity and location of the leading jaw assembly are monitored, as well as the spacing between the two jaw assemblies. In addition, a load sensor is mounted to one of the clamping jaws to measure the force being applied to the sample. All of the measured data is transmitted to the microprocessor for evaluation in determining the stress-strain characteristics of the test sample. Also, the linear motor is controlled by the microprocessor, and the velocity measurements provide real-time data to continuously determine whether the desired test speed is being maintained. A closed loop between the microprocessor, the linear encoder measuring velocity, and the linear motor can be formed to accordingly adjust and maintain the desired test velocity.

In conducting a test run, a sample is caused to be gripped by both clamping jaws with the jaw assemblies being coupled together. A desired test velocity is inputted into the microprocessor. The use of a linear motor advantageously allows for a wide range of test velocities which may be selected being in the range of 0.05 meter/min to 5 meters/sec. Once the sample is loaded and the test velocity is selected, the test is initiated and the linear motor accelerates the coupled jaw assemblies to the test velocity. With the test velocity having been achieved, the test run is initiated upon the follower jaw assembly engaging the catch mechanism and being caused to be instantaneously stopped. The movement of the leading jaw assembly, however, is unhindered. Consequently, the leading jaw assembly moves away from the follower jaw assembly, thus causing the sample to elongate. Data is acquired by the linear encoders and the load sensor and transmitted to the microprocessor for evaluation. The test is completed upon the leading jaw assembly having translated the full length of the test run. Depending on the elasticity of the sample being tested, the sample may have failed during the course of the test. Acquired data is used to determine the stress-strain characteristics of the sample at the test velocity, from which the modulus of elasticity may be determined. Subsequent tests may be performed on the same material to determine the effects of different velocities on the modulus of elasticity of the sample material being evaluated.

In one embodiment of the invention, the test is initiated without tension being applied to the sample. Alternatively, one or both of the clamping jaws may be formed to be moveable relative to the respective jaw assemblies to allow for pre-tensioning of the sample prior to initiation of the test run. As further modifications, the apparatus can be disposed to have the rail vertically or horizontally aligned.

These and other features of the invention will be better understood through a study of the following detailed description and accompanying drawings.

BRIEF DESCRIPTION OF THE DRAWINGS

FIG. 5 is a view similar to FIG. 2 but showing the jaw assemblies in position at the onset of a test run.

FIG. 6 is a view similar to FIG. 5 but with the jaw assemblies being in position at the completion of a test run.

DETAILED DESCRIPTION OF THE INVENTION

Figure 1:
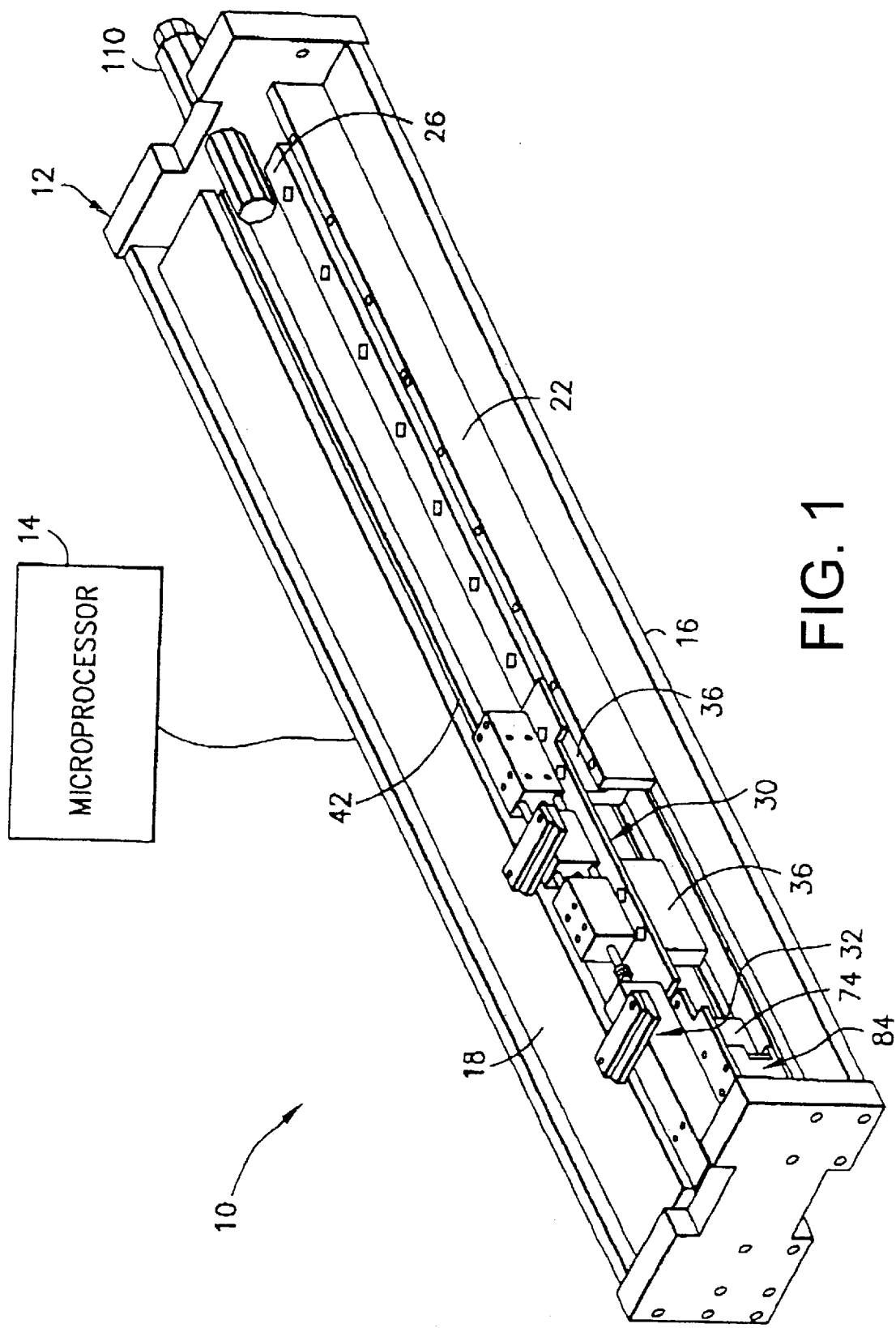
FIG. 1 is a perspective view of the system of the subject invention.

Referring generally to FIG. 1, a system 10 is shown for evaluating the tensile characteristics of a sample under dynamic conditions. Specifically, the system 10 evaluates a sample which is caused to travel at a selected test velocity under tensile loading. The system 10 includes an apparatus 12 and a microprocessor 14.

Figure 2:
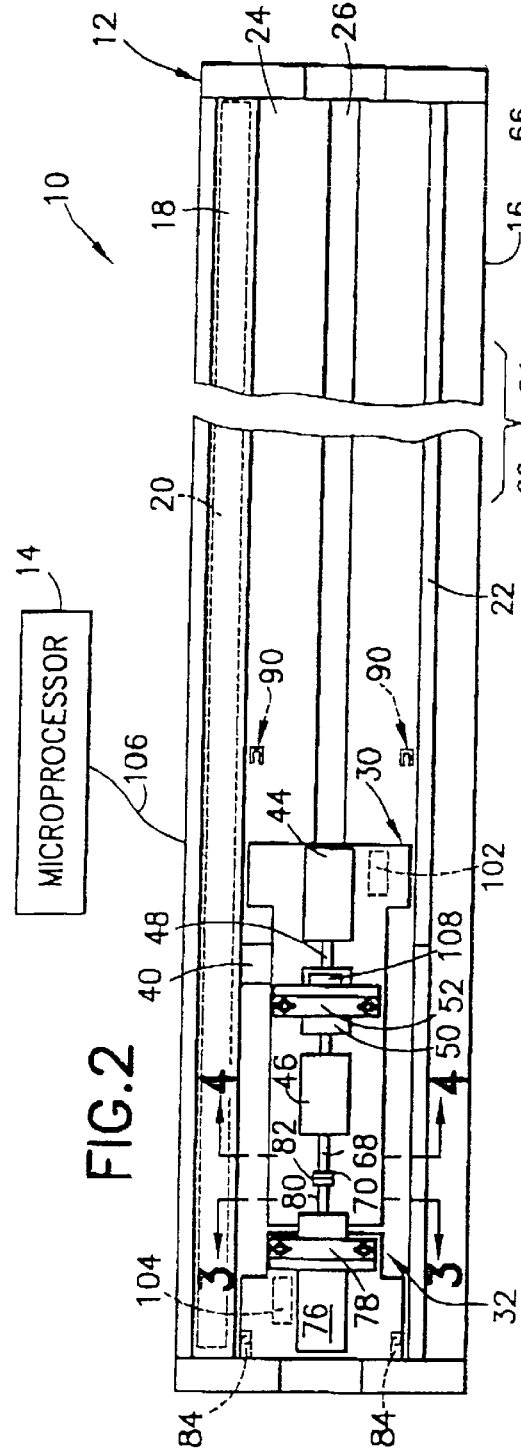
FIG. 2 is a top view of the apparatus of the subject invention.
Figure 4:
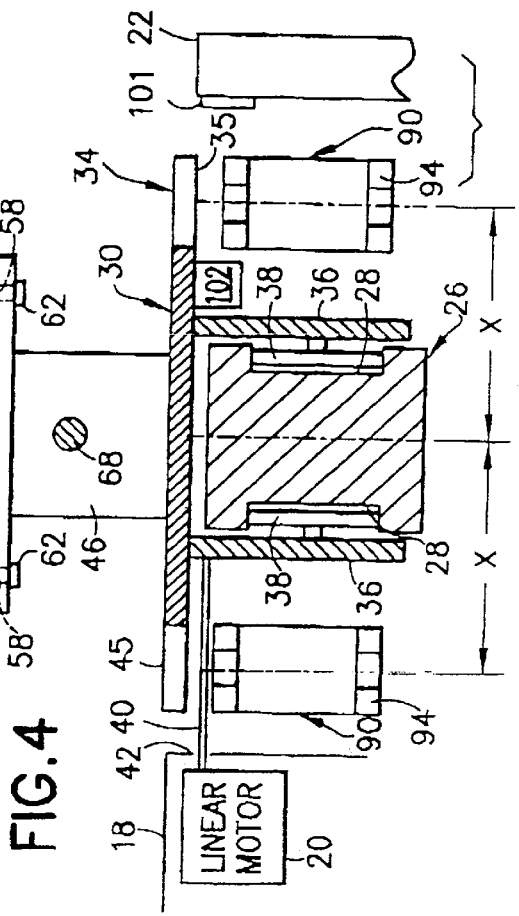
FIG. 4 is a partial cross-sectional view taken along line 4—4 of FIG. 2.
Figure 3:
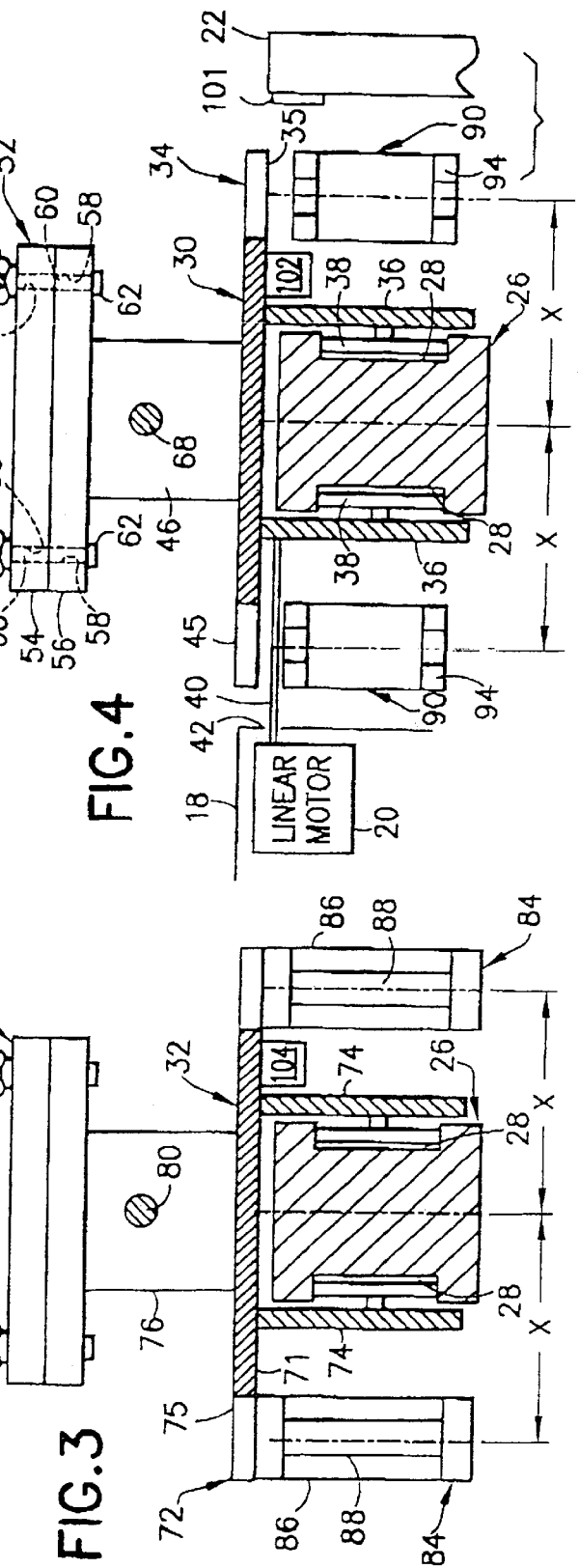
FIG. 3 is a partial cross-sectional view taken along line 3—3 of FIG. 2.

Referring generally to FIGS. 1–4, the apparatus 12 is formed with an elongated housing 16 having a raised portion 18 which extends the entire length thereof. A linear motor 20 is enclosed within the raised portion 18. An upstanding wall 22 is provided with the housing 16 which is spaced from the raised portion 18 to define a trough 24. A rail 26 is mounted to the housing 16 and disposed between the raised portion 18 and the wall 22. It is preferred that the rail 26 be precision machined to be as straight as possible and provided with a fine finish. As shown in FIGS. 3 and 4, the rail 26 has a generally I-shaped cross-section with channels 28 being formed therein along the entire length of the rail 26.

A leading jaw assembly 30 and a follower jaw assembly 32 are mounted onto the rail 26 such that both of the jaw assemblies 30, 32 can translate along the length of the rail 26. Referring specifically to the leading jaw assembly 30, a base plate 34 is provided having a bottom surface 35 to which four downwardly extending linear slides 36 are mounted. Each of the linear slides 36 is formed with at least one roller 38 formed to roll within one of the channels 28 of the rail 26. The linear slides 36 are arranged such that a pair of the slides 36 is found on each side of the rail 36 in a spaced-apart arrangement. The interengagement of the rollers 38 with the channels 28 limits movement of the leading jaw assembly 30 in directions perpendicular to the longitudinal axis of the rail 26. The leading jaw assembly 30 is coupled to the linear motor 20 by a bracket 40 which passes through a slot 42 formed in the raised portion 18. As can be seen in FIG. 1, the slot 42 extends the full length of the raised portion 18, thus allowing for the linear motor 20 to drive the leading jaw assembly 30 along substantially the full length of the rail 26.

Support blocks 44 and 46 are rigidly mounted to the top surface 45 of the base plate 34 at spaced-apart locations. Guides 48 extend between the support blocks 44 and 46 to which clamp support 50 is mounted. In one variation of the invention, the clamp support 50 may be rigidly fixed relative to the base plate 34. Alternatively, the clamp support 50 may be mounted to allow movement thereof to provide tension to a sample prior to a test run, as described below. A clamping jaw 52 is secured to the clamp support 50. Any clamping jaw design known to those skilled in the art which may tightly engage the end of a sample may be used with the subject invention. A simple, but effective, design is shown in the figures as a possible design which may be utilized. In particular, the clamping jaw 52 is formed with two separate, upper and lower rectangular plates 54 and 56, each having a pair of apertures 58 being formed therethrough. Two bolts 60 are disposed in the apertures 58, respectively, with the heads of the bolts 62 being in pressing engagement with the lower plate 56. Wing nuts 64 are threaded onto the free ends 66 of the bolts 60. To mount a sample to the clamping jaw 52, the wing nuts 64 are loosened sufficiently to allow the upper plate 54 to be lifted from and separated from the lower plate 56. An end of the sample is disposed between the plates 54 and 56, and the wing nuts 64 are tightened.

The leading jaw assembly 30 is also formed with a shaft 68 extending from the support block 46. A detachable coupling element 70 is secured to the shaft 68. The structure and function of the coupling element 70 is described below.

The follower jaw assembly 32 has many of the same structural elements as the leading jaw assembly 30. Specifically, the follower jaw assembly 32 has a base plate 72, two linear slides 74 secured to the bottom surface 71 of the base plate 72, a support block 76 rigidly mounted to the top surface 75 of the base plate 72, a clamping jaw 78, and a shaft 80 extending from the support block 76 to which a detachable coupling element 82 is mounted. The detachable coupling element 82 is aligned to cooperate with the detachable coupling element 70. The description of these elements is generally the same as set forth with respect to the leading jaw assembly 30. As is readily apparent, the follower jaw assembly 32 is capable of translation along the length of the rail 26 with the clamping jaw 78 securely engaging an end of a sample to be tested.

Figure 8:
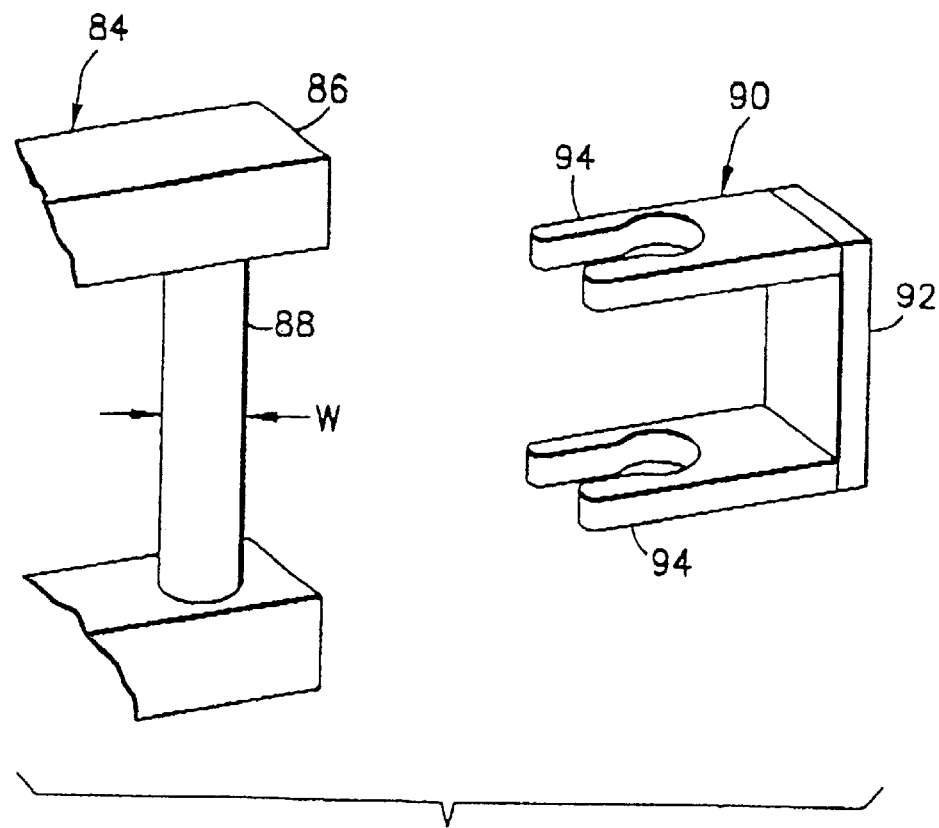
FIG. 8 is a schematic of a dowel assembly found on the follower jaw assembly prior to engaging a catch assembly.

The follower jaw assembly 32 is, however, provided with dowel assemblies 84, which are not found on the leading jaw assembly 30 and are used to cause instantaneous stopping of the follower jaw assembly 84 in cooperation with catch assemblies, described below. Referring to FIG. 3, the dowel assemblies 84 are mounted to the bottom surface 71 of the base plate 72 and each includes a bracket 86 which supports a dowel 88, as most clearly shown in FIG. 8. The dowel assemblies 84 are mounted such that the central longitudinal axis of each of the dowels 88 is located a distance "x" from the center of the rail 26.

Figure 7:
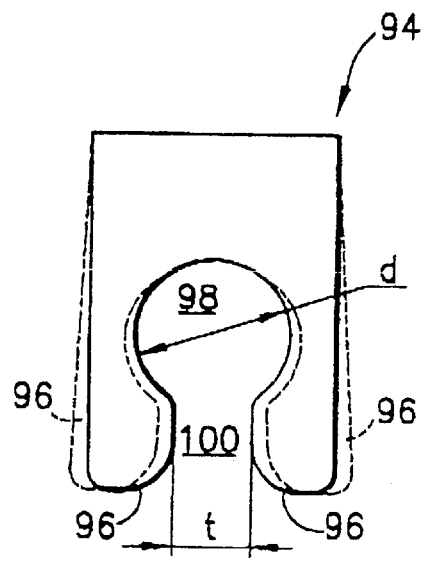
FIG. 7 is a top view of a catch member used with the subject invention.

The apparatus 12 is provided with two catch assemblies 90 which are located on the opposite sides of the rail 26, as shown in FIG. 2. Each of the catch assemblies 90 has a general U-shape defined by an upstanding bracket 92 and spaced-apart, horizontally aligned catch members 94, as most clearly shown in FIG. 8. Referring to FIG. 7, each of the catch members 94 has two arms 96 shaped to define an aperture 98 which extends continuously from an open throat 100. The dowels 88 of the follower jaw assemblies 32 are formed to define a cross-sectional diameter of "w", whereas the apertures 98 of the catch members 94 are each formed with a diameter "d" which is equal to or less than the diameter "w" of the dowels 88. In addition, the throat 100 is formed with varying widths, wherein the smallest width "t" is less than the diameter "d". The catch members 94 are to be made from a resilient material so that the arms 96 may be urged apart to increase the width "t", as shown in dashed lines in FIG. 7. Preferably, the catch members 94 are formed from nylon.

Referring to FIG. 4, the catch assemblies 90 are located so that the center of the apertures 98 formed in the catch members 94 are each spaced the distance "x", defined above with respect to the dowels 88, from the rail 26. With this spacing, the catch assemblies 90 are located to latch onto the dowels 88 and prevent any subsequent movement of the follower jaw assembly 32. Specifically, with the follower jaw assembly 32 translating along the rail 26 in the direction of the catch assemblies 90, the dowels 88 will be urged between the arms 96 of the catch members 94. Due to the resiliency of the material forming the catch members 94, the force of movement of the follower jaw assembly 32 will urge the arms 96 apart with the dowels 88 being urged into the apertures 98. The resiliency of the catch members 94 will then also cause the arms 96 to return to their respective original states. As is readily appreciated, further movement of the dowels 88, and thus the follower jaw assembly 32, would be prevented in the original direction of movement. Also, movement in other directions, caused by rebounding of the dowels 88 against the catch members 94, is also restricted due to the shape of the arms 96.

It is desired that the follower jaw assembly 32 have a perfect inelastic collision with the catch assemblies 90 so that the follower jaw assembly 32 is instantaneously stopped without subsequent movement. The structure of the dowel assemblies 84 and the catch assemblies 90 provides one method of achieving a near perfect, or better, inelastic collision. However, other cooperating structures known in the prior art may be used to instantaneously stop the follower jaw assembly 32 without subsequent movement.

As can be seen in FIG. 4, the leading jaw assembly 30 is shaped and dimensioned to altogether avoid engaging the catch assemblies 90. Likewise, the bracket 40 is positioned to avoid engagement with the catch assemblies 90. Thus, movement of the leading jaw assembly 30 is unhindered by the catch assemblies 90.

The apparatus 12 is further provided with various data collection sensors. For example, optical sensors 102 and 104, such as linear encoders, are respectively mounted to the leading jaw assembly 30 and the follower jaw assembly 32. The optical sensor 102 is disposed to face the wall 22 onto which a scale 101 or other indicia is secured. The optical sensor 102 is adapted to sense both the position of the leading jaw assembly 30 relative to the rail 26, as well as, determine the rate of translation of the leading jaw assembly 30 along the rail 26. The optical sensor 104 mounted to the follower jaw assembly 32 is disposed to sense a scale (not shown) secured to the raised portion 18 to monitor the position of the follower jaw assembly 32. Data collected by both of the optical sensors 102 and 104 is transmitted to the microprocessor 14 through a connection line 106. In addition, a force sensor 108, such as a piezoelectric force transducer, is secured to one of the clamping jaws 52 or 78. As shown in the figures, the force sensor 108 is located within the clamp support 50. The force sensor 108, however, could also be secured to the clamping jaw 78. Load measurements measured by the force sensor 108 are likewise transmitted to the microprocessor 14 via the connection line 106. The load sensor 108 must be mounted to sense the force applied only to the relevant clamping jaw 52, 78.

In setting up a test run, a predetermined length of the rail 26 is predesignated to define the test run. The test run is the distance the leading jaw assembly 30 will travel at a desired test velocity with the follower jaw assembly 32 being locked in a fixed position. Referring to FIGS. 5 and 6, the length of the test run is designated by the distance "L".

It is preferred that the microprocessor 14 not only collect data but also control the apparatus 12. In particular, it is desired that the microprocessor 14 control the linear motor 20. To enable such control, the length of the test run "L" is inputted into the microprocessor 14, as well as the desired test velocity.

Prior to initiation of the test run, the jaw assemblies 30 and 32 must be coupled together using the respective coupling elements 70 and 82. In the preferred embodiment, the coupling elements are magnets. However, other detachable couplings known in the prior art may also be utilized. The detachable coupling arrangement has to be such that it will transmit motive force from the leading jaw assembly 30 to the follower jaw assembly 32, but also will become detached upon movement of the leading jaw assembly 30 with the catch assemblies 90 engaging the follower jaw assembly 32.

With the jaw assemblies 30 and 32 being coupled together, a sample S is mounted in the clamping jaws 52 and 78. Thereafter, the microprocessor 14 is caused to initiate the test run with the linear motor 20 being actuated and caused to accelerate the leading jaw assembly 30 and the follower jaw assembly 32, via the coupling attachment between the coupling elements 70 and 82. The linear motor 20 must achieve the test velocity at the initiation of or prior to the test run. The test run is initiated with the follower jaw assembly 32 having been instantaneously stopped. FIG. 5 shows the jaw assemblies 30 and 32 being in position at the beginning of a test run with the dowel assemblies 84 engaging the catch assemblies 90. To ensure the proper test velocity is achieved during the test run, it is preferred that the test velocity be achieved prior to the initiation of the test run. Thus, it is preferred that the linear motor 20 accelerate the coupled jaw assemblies 30 and 32 to the test velocity prior to the follower jaw assembly 32 being instantaneously stopped.

Once the test velocity is achieved, it is desired that the test velocity be maintained throughout the test run. To this end, it is preferred that a closed loop be defined by the sensor 102, which senses the actual rate of translation of the leading jaw assembly 30, the microprocessor 14 and the linear motor 20.

Having achieved the desired test velocity and having the follower jaw assembly 32 being in a locked position, the leading jaw assembly 30 continues to translate at the test velocity away from the follower jaw assembly 32. As shown in FIG. 6, the coupling elements 70 and 82 become detached. As described above, the load sensor 108 is mounted to measure force applied to one of the clamping jaws 52, 78. The detachment of the coupling elements 70 and 82, as well as the engagement of the dowel assemblies 84 and the catch assemblies 90 will cause slight changes in momentum applied to the jaw assemblies 30 and 32. Since the load sensor 108 is mounted to measure load at the respective clamping jaw 52, 78, these disturbances in momentum are not sensed by the load sensor 108. Also, due to the very low compliance of the piezoelectric force transducer, the load sensor 108 will not introduce any significant position measurement error. Additionally, the linear motor 20 should be selected to have sufficient torque to maintain the test velocity through these disturbances.

As the leading jaw assembly 30 translates through the test run, the optical sensors 102 and 104, as well as the force sensor 108, accumulate real-time data which is transmitted to the microprocessor 14 for evaluation. Once the full length "L" of the test run has been traversed, the leading jaw assembly 30 is caused to decelerate and eventually stop. Depending on the elastic characteristics of the sample S, the sample S may fail, as shown in FIG. 6, or be merely elongated. The data collected by the microprocessor 14 is used to determine the stress-strain characteristics of the sample S, as well as the modulus of elasticity of the sample S.

In the method described above, the sample S is entered into the test run without being under tensile load. As an alternative, the clamping jaws 58 and 72 may be mounted to the jaw assemblies 30 and 32, respectively, to allow relative movement therebetween. In this manner, one or both of the clamping jaws 52 and 78 may be moved apart to apply a tensile load to the sample S prior to initiation of the test run. As a further modification, the movement of the clamping jaws 52 and 78 may be adapted to be controlled by the microprocessor 14. As another additional feature, a bumper 110 may be mounted to one end of the housing 16 above the rail 26. The bumper 110 is intended to cushion any possible impact the leading jaw assembly 30 may have with the housing 16. It should also be noted that, although the apparatus 12 is shown to be disposed in a generally horizontal fashion, the apparatus can operate as effectively oriented in a vertical manner.

As is readily apparent, numerous modifications and changes may readily occur to those skilled in the art, and hence it is not desired to limit the invention to the exact construction and operation, as shown and described, and accordingly all suitable modification equivalents may be resorted to falling within the scope of the invention as claimed.

What is claimed is:

1. An apparatus for testing tensile properties of a sample under dynamic conditions, said apparatus comprising:
    an elongated housing having a length and a raised portion extending the length of said housing and an upstanding wall spaced parallel from said raised portion, wherein said raised portion and said upstanding wall define a trough;
    a rail mounted to said housing disposed between said raised portion and said upstanding wall;
    first and second clamping jaws slidably mounted to said rail, said clamping jaws being formed to grippingly engage the sample;
    rate measuring sensor means for measuring a rate of sliding of at least one said clamping jaw relative to said rail;
    distance measuring sensor means for measuring distance between said clamping jaws;
    load sensor means for measuring tensile load applied to the sample; and
    a microprocessor operatively connected to the rate measuring sensor means, the distance measuring sensor means and the load sensor means for determining characteristics of sample.

2. An apparatus as in claim 1, wherein said clamping jaws are detachably coupled.

3. An apparatus as in claim 2, further comprising a motor means for forcing sliding movement of said first clamping jaw along the length of said rail.

4. An apparatus as in claim 3, further comprising a means for instantaneously stopping the sliding movement of said second clamping jaw.

5. An apparatus as in claim 4, further comprising a means for preventing rebounding of said second clamping jaw coacting with said means for instantaneously stopping.

6. An apparatus as in claim 5, wherein, said microprocessor controls said motor means thereby maintaining a test velocity.

7. An apparatus as in claim 6, wherein said sensor means are linear incoders.

8. An apparatus as in claim 6, wherein said load sensor means is a piezoelectric force transducer.

9. An apparatus as in claim 6, wherein said motor means is a linear motor.

10. An apparatus as in claim 6, wherein said first and second clamping jaws are longitudinal slidable away from each other to tension said sample prior to a test run.

11. An apparatus as in claim 6, wherein said rail is adapted to be engaged by said clamping jaws to prevent movement of said jaws in a direction perpendicular to the rail.

12. An apparatus as in claim 6, further comprising a bumper means mounted to one end of said housings above said rail to minimize impact of said jaws against said end of said housing.

13. A method for determining the tensile characteristics of a sample under dynamic conditions, the sample having opposing first and second ends, said method comprising the steps of:
    providing first and second clamping jaws formed. to grippingly engage the ends of the sample;
    causing said first clamping jaw to grippingly engage the first end of the sample;
    causing said second clamping jaw to grippingly engage the second end of the sample;
    accelerating said clamping jaws and the sample in unison to a predetermined test velocity, such that said clamping jaws and said sample are subjected to movement in unison in a selected linear direction; then
    instantaneously fixing said first clamping jaw to prevent further movement thereof without impeding the movement of the second clamping jaw; then
    continuing the movement of said second clamping jaw in said selected linear direction away from said first clamping jaw and at the test velocity; and
    measuring tensile force applied to the sample.

14. A method as in claim 13, further comprising the step of measuring velocity of said second clamping jaws.

15. A method as in claim 13, further comprising the step of measuring a distance between said clamping jaws.

16. A method as in claim 15, further comprising the step of applying tensile load to the sample prior to the step of accelerating said clamping jaws and the sample.

17. An apparatus for testing tensile properties of a sample under dynamic conditions, said apparatus comprising:
    first and second clamping means for selectively gripping spaced apart locations on the sample;
    coupling means for releasably coupling said first and second clamping means to one another;
    accelerating means for accelerating said first and second clamping means to a selected test velocity and for movement of said first and second clamping means in unison and in a selected linear direction;
    catch means mounted at least partly on said first clamping means for substantially instantaneously stopping said movement of said first clamping means after said first and second clamping means have been accelerated by the accelerating means to the selected test velocity, while permitting continued movement of said second clamping means at said test velocity; and measurement means in proximity to at least one of said first and second clamping means for measuring at least a tensile load applied to the sample after the movement of the first clamping means is stopped by the catch means.

18. An apparatus as in claim 17, wherein the coupling means comprises a magnet.

19. An apparatus as in claim 17, wherein the catch means comprises means for preventing a rebound of said first clamping means.

20. An apparatus as in claim 17, wherein the first clamping means is behind the second clamping means relative to said selected liner direction of movement.

* * * * *